United States Patent [19]

Tsuchiya et al.

[11] Patent Number: 5,836,883

[45] Date of Patent: Nov. 17, 1998

[54] MEASURING THE CHARACTERISTICS OF A SCATTERING MEDIUM

[75] Inventors: Yutaka Tsuchiya; Yutaka Yamashita, both of Hamamatsu, Japan

[73] Assignee: Technology Research Association of Medical and Welfare Apparatus, Tokyo, Japan

[21] Appl. No.: 693,480

[22] Filed: Aug. 8, 1996

[30] Foreign Application Priority Data

Aug. 8, 1995 [JP] Japan .................................. 7-202115

[51] Int. Cl.$^6$ ........................................................ A61B 5/00
[52] U.S. Cl. .............................................. 600/476; 356/39
[58] Field of Search ............................... 128/653.1, 664, 128/665, 633, 634; 356/40, 433, 39, 432; 600/407, 476, 473

[56] References Cited

U.S. PATENT DOCUMENTS

| | | | |
|---|---|---|---|
| 4,953,947 | 9/1990 | Bhagavatula | 350/96.33 |
| 5,119,815 | 6/1992 | Chance | 128/633 |
| 5,140,608 | 8/1992 | Karpol et al. | 372/101 |
| 5,386,827 | 2/1995 | Chance et al. | 128/633 |
| 5,582,169 | 12/1996 | Oda et al. | 128/633 |
| 5,606,969 | 3/1997 | Butler et al. | 128/653.1 |

FOREIGN PATENT DOCUMENTS

| | | |
|---|---|---|
| 628 804 | 12/1994 | European Pat. Off. . |
| 636 876 | 2/1995 | European Pat. Off. . |
| 656 537 | 6/1995 | European Pat. Off. . |
| 4-191642 | 7/1992 | Japan . |
| 93/13395 | 7/1993 | WIPO . |

*Primary Examiner*—Marvin M. Lateef
*Assistant Examiner*—Eleni Mantis Mercader
*Attorney, Agent, or Firm*—Cushman Darby & Cushman IP Group of Pillsbury Madison & Sutro LLP

[57] ABSTRACT

Apparatus for measuring characteristics of a scattering medium. A light source irradiates the medium to be measured with a plurality of measurement light beams. A wavelength selector unit selectively extracts diffused light having a particular wavelength. A photodetector unit measures a time response characteristic of the diffused light. The signal processing system drives the light source so as to sequentially cause measurement light beams to be incident on the scattering medium and controls a measurement action of the photodetector unit while analyzing the time-response characteristics so as to calculate the internal information in the scattering medium.

5 Claims, 8 Drawing Sheets

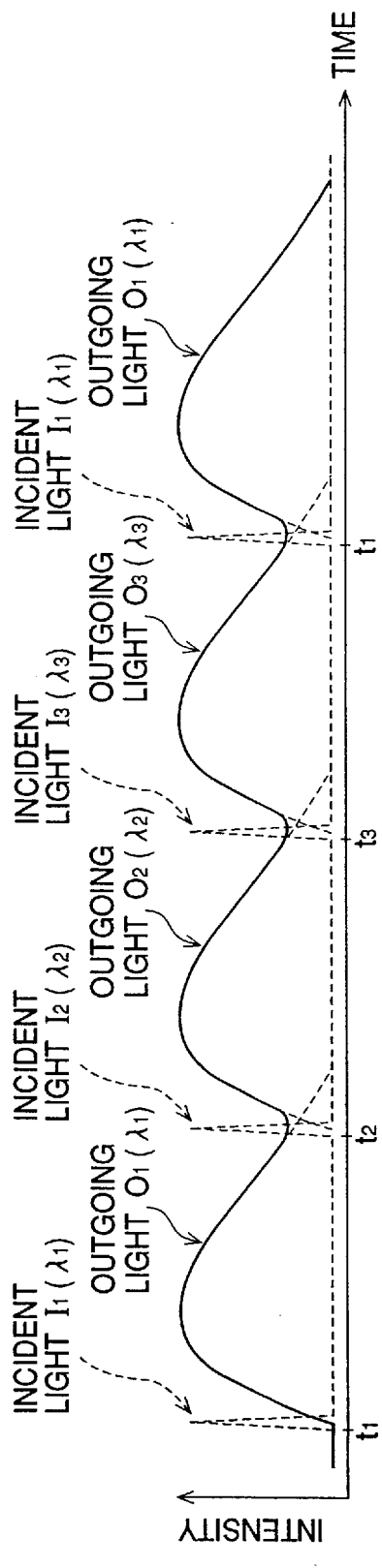

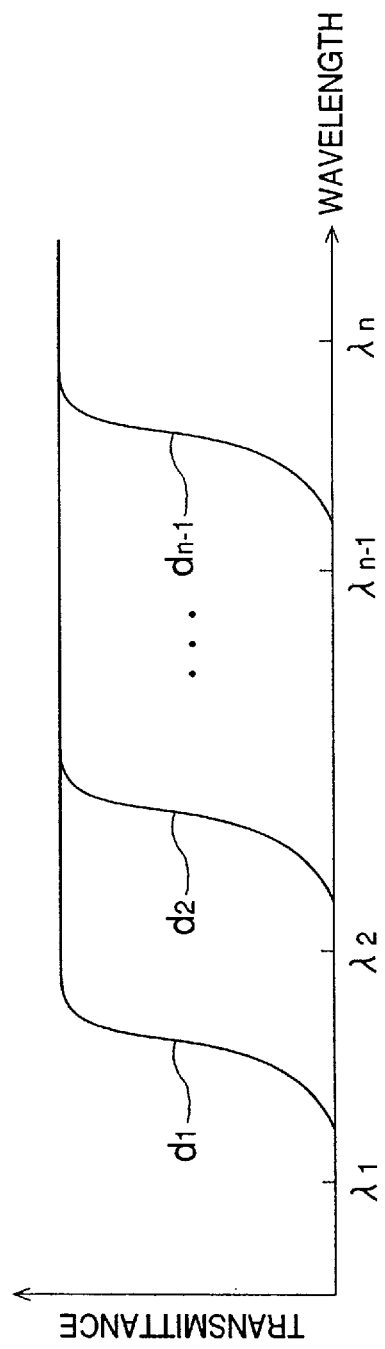

MEASURING THE CHARACTERISTICS OF A SCATTERING MEDIUM

BACKGROUND OF THE INVENTION

1. Field of the Invention

The present invention relates to an apparatus for noninvasively measuring internal characteristics of a scattering media. It is particularly useful in medical and scientific, applications. More specifically, the present invention relates to a measurement apparatus which measures optical scattering characteristics and/or optical absorption characteristics of a scattering media such as living tissues, thereby obtaining such data as those concerning changes in various characteristic values over time and their spatial distribution.

2. Related Background Art

Conventionally, in order to measure optical scattering and optical absorption characteristics of a media such as living tissues, it has been known to irradiate the medium to be measured with measurement light, detect the diffused light, and then analyze the time-response characteristic of the detected light. In general, in order to perform a multicomponent measurement with respect to the scattering medium, a measurement apparatus used for such a technique is equipped with a light source for generating pulse-like light beams having at least two wavelengths. For such two wavelength irradiating methods, there have been known two techniques for driving the light source, namely, sequential lighting and alternate lighting.

As shown in FIG. 1, when a light source driven by the sequential lighting technique is used, for example, in order to cause measurement light beams having two different wavelengths $\lambda_1$ and $\lambda_2$ to be incident on a subject scattering medium, the scattering medium is irradiated with the measurement light beam having the wavelength of $\lambda_1$ emitted by the light source as a few pulses of incident light $I_i$ in the first place. Then, the diffused light having the wavelength of $\lambda_1$ emitted from the scattering medium are sequentially detected as outgoing light $O_1$. Subsequently, after the wavelength setting for the light beam with respect to the light source generating the $\lambda_1$-wavelength light beam is changed over to the wavelength of $\lambda_2$ the scattering medium is irradiated with the light beam having the wavelength of $\lambda_2$ emitted by the light source as a few pulses of incident light $I_2$. Thereafter, the diffused light having the wavelength of $\lambda_2$ emitted from the scattering medium are sequentially detected as outgoing light $O_2$.

As shown in FIGS. 2A and 2B, when a set of light sources driven by the alternate lighting technique is used, for example, in order to cause measurement light beams having two different wavelengths $\lambda_1$ and $\lambda_2$ to be incident on a subject scattering medium, the scattering medium is irradiated with the light beam having the wavelength of $\lambda_1$ emitted by one of the light sources as incident light $I_1$. Then, when a predetermined period has passed after the irradiation with the incident light $I_1$, the scattering medium is irradiated with a light beam having the wavelength of $\lambda_2$ which is emitted by the other light source. Thereafter, the diffused light having the wavelength of $\lambda_1$ emitted from the scattering medium is detected as outgoing light $O_1$. Then, the diffused light having the wavelength of $\lambda_2$ emitted from the scattering medium is detected as outgoing light $O_2$.

When a sequential lighting technique such as that shown in FIG. 1 is used in the above-mentioned measurement apparatus to irradiate a scattering medium with the light beams having wavelengths different from each other, the interval of the pulse light irradiation must be longer than the duration of diffused light emitted from the scattering medium. Otherwise diffused light piles up. Therefore, the time required for measuring the time-response characteristic of the diffused light emitted from the scattering medium increases in proportion to the number of kinds of wavelengths which is set for the measurement light beams. On the other hand, when an alternate lighting technique such as that shown in FIGS. 2A and 2B is used, there is a problem that the upper limits concerning the frequencies for generating the measurement light beams having different wavelengths are restricted due to an interval $t_1$ required between the outgoing light $O_1$ and the outgoing light $O_2$ in order to prevent the diffused light having the wavelengths $\lambda_1$ and $\lambda_2$ from being mixed with each other, thereby making it difficult to sufficiently shorten the measurement time.

SUMMARY OF THE INVENTION

In view of the foregoing problems, the object of the present invention is to provide a measurement apparatus in which the dependency of the measurement time on the number of kinds of wavelengths of the measurement light beams can be alleviated, thereby making it possible to sufficiently shorten the time required for measuring the time-response characteristic of the diffused light.

The measurement apparatus for internal information in a scattering medium in accordance with the present invention comprises:

(a) a light source which emits a plurality of measurement light beams having a plurality of wavelengths different from each other;

(b) an irradiation light guide for causing the measurement light beams to be incident on the scattering medium;

(c) a wavelength selector unit which selectively extracts diffused light having an individual wavelength from diffused light corresponding to the measurement light beams which have been diffusively propagated through the scattering medium;

(d) a photodetector unit for measuring a time-response characteristic of the diffused light extracted by the wavelength selector unit; and (e) a signal processing system which drives the light source so as to sequentially cause the measurement light beams to be incident on the scattering medium respectively with emission timings (points of time) different from each other, and which controls a measurement action of the photodetector unit corresponding to the emission timings such that time-response characteristics of the diffused light are sequentially measured, while analyzing the time-response characteristics measured by the photodetector unit so as to calculate the internal information in the scattering medium.

The above-mentioned wavelength selector unit preferably comprises an acousto-optic modulator. The acousto-optic modulator generates an ultrasonic wave (vibration) based on a control signal output from the above-mentioned signal processing system and changes the wavelength of the above-mentioned ultrasonic wave in synchronization with the emission timing of the measurement light beam so as to diffract the diffused light by a deflection angle which corresponds to the ratio of the wavelength of the diffused light to that of the ultrasonic wave. In this case, the above-mentioned photodetector unit preferably comprises a photodetector. The photodetector is one which, based on a control signal output from the above-mentioned signal processing system, detects the diffused light which has been diffracted by a predetermined deflection angle by the above-mentioned acousto-optic modulator and then converts the diffused light thus detected so as to effect a time-resolved measurement.

Alternatively, the above-mentioned wavelength selector unit may comprise a plurality of dichroic mirrors as follows. Namely, such dichroic mirrors are those which are serially disposed in an optical path of the above-mentioned diffused light guided from the scattering medium to the photodetector unit such that their threshold wavelengths (threshold wavelength being a wavelength at the boundary between the wavelengths of light to be reflected by the mirror and those of light to be transmitted through the mirror) are respectively positioned between neighboring wavelengths of the above-mentioned diffused light (in ascending or descending order) and set in ascending or descending order. The photodetector unit preferably comprises a plurality of interference filters and a plurality of photodetectors. Namely, such interference filters respectively have transmittance center wavelengths coinciding with wavelengths of the diffused light entering the interference filters from the dichroic mirrors, whereas such photodetectors respectively, based on a control signal output from the signal processing system, detect the diffused light entering the photodetectors from the interference filters and then convert the diffused light thus detected so as to effect a time-resolved measurement.

Preferably, the measurement apparatus of the present invention further comprises (f) a detection light guide for guiding the diffused light which has been diffusively propagated through the scattering medium to the wavelength selector unit, and (g) an optical shaper which is optically connected to the detection light guide and converges the diffused light so as to be guided to the wavelength selector unit.

Also, the light source in accordance with the present invention is preferably a group of light sources which respectively emit, based on a control signal output from the signal processing system, the measurement light beams having a plurality of wavelengths whose number is not smaller than that of kinds of optical absorbent components contained in the scattering medium and which have absorption coefficients different from each other with respect to the optical absorbent components.

In the measurement apparatus of the present invention, a light source or light sources emit, based on a control signal output from the signal processing system, measurement light beams having wavelengths different from each other at emission timings different from each other in a periodic manner. These measurement light beams sequentially emitted from the light source(s) radiate into a scattering medium by way of the irradiation light guide and, after being diffusively propagated through the scattering medium, sequentially entered into the wavelength selector unit.

At this time, the wavelength selector unit selectively extracts, in a sequential manner, diffused light having a particular wavelength from diffused light corresponding to the incident measurement light beams and guides thus extracted diffused light to the photodetector unit. Accordingly, even when the diffused light sequentially emitted from the scattering medium contain mutually-interfered light components (diffused light having other wavelengths) since they have, due to random scattering within the scattering medium, a pulse width greater than that at the time of emission, the diffused light sequentially emitted from the wavelength selector unit do not contain such mutually-interfered light components.

As a result, since no base-line shift occurs, due to the mutually-interfered light components, in the diffused light sequentially entering the photodetector unit, even when the interval of the emission timings for the measurement light beams is shortened to such an extent that the diffused light emitted from the scattering medium may contain the mutually-interfered light components, the time-response characteristic of the diffused light can be accurately measured by the signal processing system. Then, as the signal processing system analyzes the time-response characteristic of the diffused light measured by the photodetector unit, internal information in the scattering medium such as its optical scattering and optical absorption characteristics can be accurately calculated.

According to the measurement apparatus of the present invention, it is unnecessary for the emission timings for the measurement light beams to have such a large interval that the diffused light emitted from the scattering medium does not contain the mutually-interfered light components. Therefore, the time required for measuring the time-response characteristic of the diffused light with respect to the scattering medium can be greatly shortened as compared with the conventional techniques.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 7 is a graph showing temporal waveforms of measurement light beams entering a scattering medium with their wavelengths being sequentially changed for every single pulse and the diffused light emitted from the scattering medium in the measurement apparatus shown in FIG. 3;

FIG. 9 is a graph showing wavelength-transmittance characteristics at a plurality of dichroic mirrors into which diffused light emitted from a scattering medium sequentially enter in the measurement apparatus shown in FIG. 8.

DESCRIPTION OF THE PREFERRED EMBODIMENTS

Figure 1:
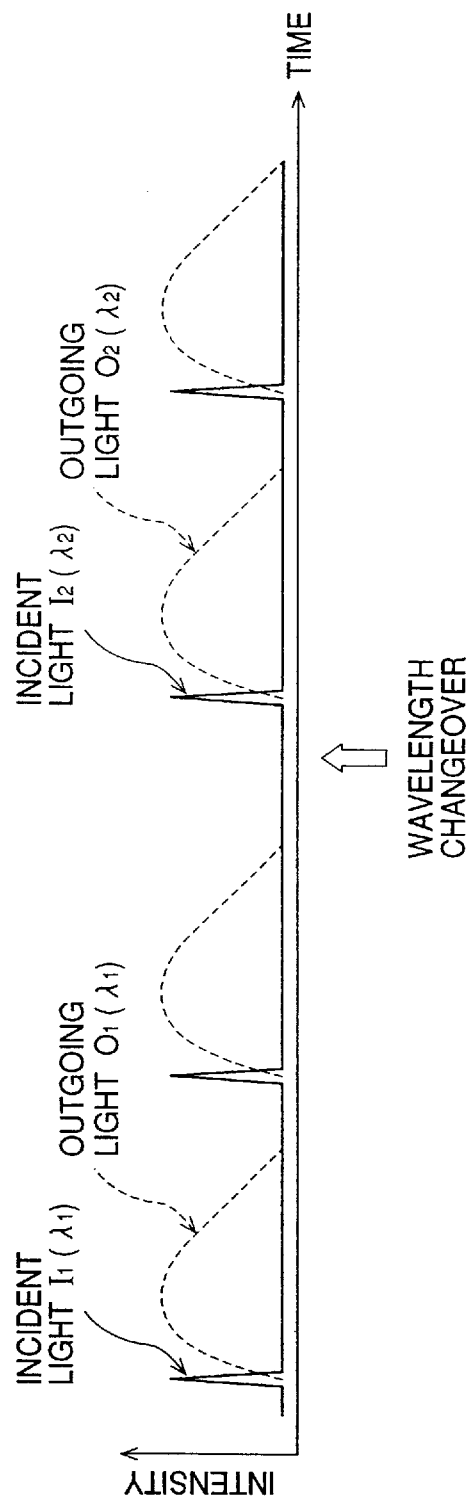
FIG. 1 is a graph showing temporal waveforms of measurement light beams which enter a scattering medium with their wavelengths being sequentially changed in every few pulses and the diffused light emitted from the scattering medium in a conventional measurement apparatus.
Figure 2:
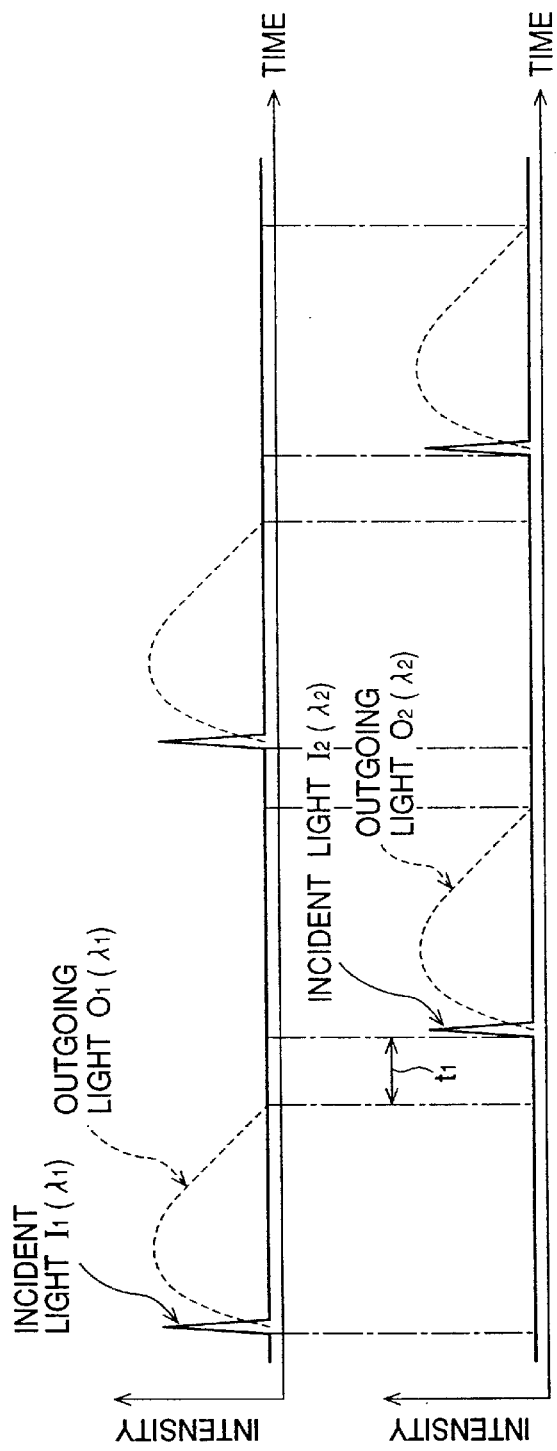
FIGS. 2A and 2B are each graphs showing temporal waveforms of measurement light beams which alternately (with a phase shift corresponding to a half wavelength) enter from a set of light sources into a scattering medium and have wavelengths (A: $\lambda_1$; B: $\lambda_2$) different from each other and the diffused light emitted from the scattering medium in another conventional measurement apparatus.

In the following, the configuration and effects of some embodiments concerning the measurement apparatus of the present invention will be explained in detail with reference to FIGS. 3 to 9. Identical elements are referred to by the identical reference numerals without repeating their explanations.

First Embodiment

Figure 3:
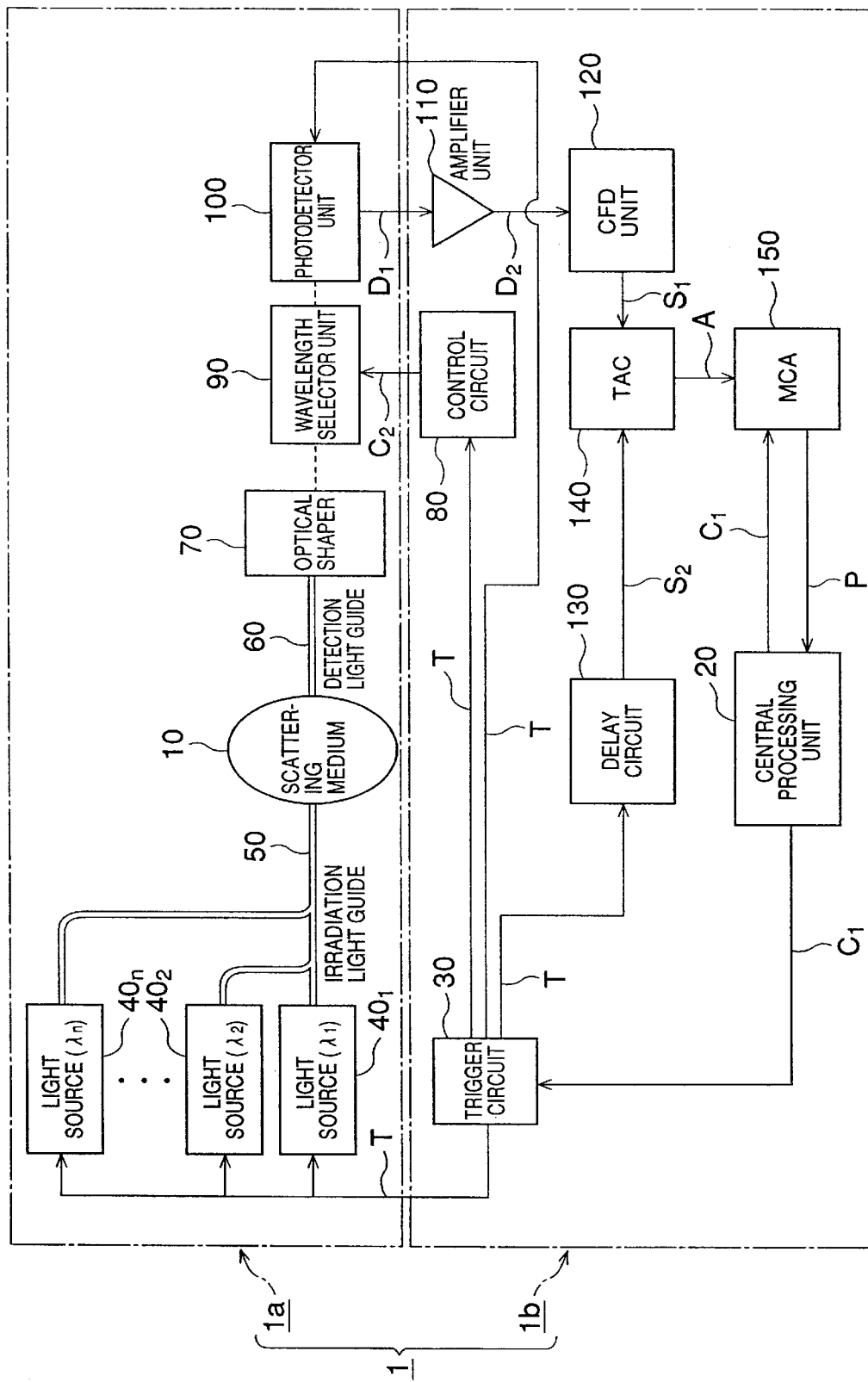
FIG. 3 is a block diagram showing a configuration of the measurement apparatus in accordance with an embodiment of the present invention.

As shown in FIG. 3, a measurement apparatus 1 of this embodiment is provided with an optical system 1a, which irradiates a scattering medium 10 with a predetermined light beam and then detects the diffused light emitted from the scattering medium 10, and a signal processing system 1b which controls actions of various instruments constituting this optical system 1a so as to analyze a time-response characteristic of the diffused light. Here, the scattering medium 10 is a living tissue which is disposed as a measurement subject from which various characteristics concerning optical scattering and optical absorption characteristics are to be measured and contains (n−1) kinds of optical absorbent components $A_1$ to $A_{n-1}$ which are different from each other. These (n−1) kinds of optical absorbent components $A_1$ to $A_{n-1}$ have absorbance values which are relatively large with respect to light having a predetermined range of wavelength and different from each other. For example, with respect to hemoglobin, myoglobin, or the like, light having a wavelength within the range of about 700 to 1,000 nm is preferable. Here, n is an integer not less than 2.

The optical system 1a comprises first to n-th light sources $40_1$ to $40_n$ which sequentially emit measurement light beams respectively having n kinds of wavelengths $\lambda_1$ to $\lambda_n$ at predetermined emission timings different from each other; an irradiation light guide (optical fiber) 50 which irradiates a predetermined light-entering position of the scattering medium 10 with the measurement light beams sequentially emitted from these first to n-th light sources $40_1$ to $40_n$; a detection light guide (optical fiber) 60 which detects the diffused light sequentially emitted from a predetermined light-output position of the scattering medium 10; an optical shaper 70 which shapes the pattern of the diffused light sequentially guided by the detection optical fiber 60; a wavelength selector unit 90 which selectively extracts the diffused light having a wavelength of one of the n kinds of wavelengths $\lambda_1$ to $\lambda_n$, in a sequential manner, from among the diffused light sequentially entering from the optical shaper 70; and a photodetector unit 100 which converts the diffused light extracted by the wavelength selector unit 90 into a detection signal $D_1$ which is then output.

Also, the signal processing system 1b includes a central processing unit 20 which outputs a control signal $C_1$ indicative of a start timing for measuring the scattering medium 10; a trigger circuit 30 which outputs, based on the control signal $C_1$ output from the central processing unit 20, a trigger signal T which becomes an index for the emission timings for the first to n-th light sources $40_1$ to $40_n$; a control circuit 80 which outputs, based on the trigger signal T output from the trigger circuit 30, a control signal $C_2$ indicative of the driving state of the wavelength selector unit 90; and an amplifier unit 110 which amplifies the detection signal $D_1$ output from the photodetector unit 100 and outputs thus amplified detection signal $D_2$.

Further, the signal processing system 1b includes a constant-fraction discriminator (CFD) unit 120 which detects the level of the detection signal $D_2$ output from the amplifier unit 110 and thereby outputs a start signal $S_1$; a delay circuit 130 which outputs a stop signal $S_2$ which is delayed by a predetermined time with respect to the trigger signal T output from the trigger circuit 30; a time-to-amplitude converter (TAC) 140 which outputs a time-correlated signal A having an amplitude proportional to the difference in time between the start signal $S_1$ and the stop signal $S_2$ respectively output from the CFD unit 120 and the delay circuit 130; and a multi-channel analyzer (MCA) 150 which is actuated, based on the control signal $C_1$ output from the central processing unit 20, so as to output time spectrum data P corresponding to the time-correlated signal A output from the TAC 140.

Here, the central processing unit 20 is a computer for control and analysis which are actuated on the basis of a predetermined measurement program which has been set up beforehand. The central processing unit 20 outputs the control signal $C_1$ to drive each of the trigger circuit 30 and MCA 150, while analyzing the time spectrum data P output from the MCA 150 to calculate, for example, the optical absorption coefficient, optical scattering coefficient, and optical absorbent component concentration of the scattering medium 10.

The trigger circuit 30 generates, based on the information indicative of the measurement start timing contained in the control signal $C_1$ output from the central processing unit 20, the trigger signal T which becomes an index for emission timings of the measurement light beams respectively having the n kinds of wavelengths $\lambda_1$ to $\lambda_n$. This trigger circuit 30 outputs the trigger signal T so as to drive each of the first to n-th light sources $40_1$ to $40_n$, control circuit 80, photodetector unit 100, and delay circuit 130.

The first to n-th light sources $40_1$ to $40_n$ are laser diodes which respectively pulse-oscillate the measurement light beams having the n kinds of wavelengths $\lambda_1$ to $\lambda_n$ with a period τ. Among these first to n-th light sources $40_1$ to $40_n$, emission timing $t_{oi}$ of the i-th light source $40_i$ is defined with respect to input timing $t_0$ of the trigger signal T from the trigger circuit 30 by the following equation (1):

$$t_{oi}=t_0+\tau\cdot\{m+(i-1)/n\} \quad (1)$$

wherein i is an integer not less than 1 but not more than n and m is an integer.

Here, the measurement light beams having the n kinds of wavelengths $\lambda_1$ to $\lambda_n$, selected are those exhibiting absorbance values (absorption coefficients) which are relatively large with respect to the (n−1) kinds of the optical absorbent components $A_1$ to $A_{n-1}$, which are contained in the scattering medium 10, and different from each other.

The irradiation light guide 50 is an n-branched optical fiber which turns the measurement light beams sequentially emitted from the first to n-th light sources $40_1$ to $40_n$ into measurement light beams which are arranged in time series and have been subjected to a cyclic wavelength conversion with their wavelengths being sequentially changed over for every single pulse. It irradiates the scattering medium 10 with the measurement light beam in the form of a spot. The detection light guide 60 is an optical fiber for guiding the diffused light, which has been diffusively propagated through the scattering medium 10 and sequentially emitted therefrom, to the optical shaper 70. The optical shaper 70 is constituted by a refractive lens or lens group which converges the diffused light sequentially emitted from the detection light guide 60. Thus converged diffused light is subsequently guided to the wavelength selector unit 90.

Preferably, two kinds of light-entering position to light-output position distances $P_1$ and $P_2$ are set as physical distance between the light-entering position of the scattering medium 10 at which an end of the irradiation light guide 50 is disposed and the light-output position at which an end of the detection light guide 60 is disposed. Accordingly, at least one of the irradiation light guide 50 and the detection light guide 60 is disposed so as to be movable with respect to the surface of the scattering medium 10.

The control circuit 80 outputs the control signal $C_2$ to the wavelength selector unit 90 in synchronization with the input timing $t_0$ of the trigger signal T output from the trigger circuit 30. The control circuit 80 outputs the control signal $C_2$ so as to drive the wavelength selector unit 90 such that ultrasonic waves having n kinds of wavelengths $\pi_1'$ to $\lambda_n'$ different from each other are generated as being changed over at a predetermined time ($\tau/n$). The n kinds of wavelengths $\lambda_1'$ to $\lambda_n'$ in the ultrasonic waves are defined with respect to the n kinds of wavelengths $\lambda_1$ to $\lambda_n$ in the measurement light beams, for example, by the following equation (2):

$$\lambda_1'/\lambda_1 = \lambda_2'/\lambda_2 = \ldots = \lambda_n'/\lambda_n = c \qquad (2)$$

wherein c is a constant.

The wavelength selector unit 90 is an acousto-optic modulator (AOM) which changes the optical refractive index on the basis of vibration of an ultrasonic wave so as to diffract incident light by deflection angle θ which substantially coincides with the ratio of the wavelength of the incident light to that of the ultrasonic wave. In response to the information contained in the control signal $C_2$ output from the control circuit 80 indicative of the wavelength of the ultrasonic wave, the wavelength selector unit 90 generates the vibration of the ultrasonic wave. During period $p_j$ between emission timing $t_j$ for the measurement light beam having a wavelength of $\lambda_j$ at the j-th light source $40_j$ and emission timing $t_{j+1}$ for the measurement light beam having a wavelength of $\lambda_{j+1}$ at the (j+1)-th light source $40_{j+1}$, the wavelength selector unit 90 generates an ultrasonic wave having wavelength $\pi_j'$. Here, j is an integer not less than 1 but not more than n, $t_{n+1}=t_1$, and $p_{n+1}=p_1$. Then, the wavelength selector unit 90 sequentially diffracts, by the deflection angle θ, the diffused light sequentially output from the optical shaper 70. The deflection angle θ, by which the diffused light is subjected to Bragg diffraction, is defined with respect to the ratio c of the n kinds of wavelengths $\lambda_1$ to $\lambda_n$ in the diffused light to the n kinds of wavelengths $\lambda_1'$ to $\lambda_n'$ in the ultrasonic waves by the following equation (3):

$$\theta = 2\sin^{-1}(c/2) \qquad (3)$$

The photodetector unit 100 is a photomultiplier tube which, based on the trigger signal T output from the trigger circuit 30, detects the diffused light sequentially entering it from the wavelength selector unit 90 after being diffracted by the deflection angle θ and converts it, thereby generating the detection signal $D_1$. In order to favorably detect each kind of the diffused light having one wavelength of the n kinds of wavelengths $\lambda_1$ to $\lambda_n$, the photodetector unit 100 preferably has a relatively high spectral sensitivity and gain. Also, it preferably has a frequency response as high as possible in order to favorably perform the time-resolved measurement of the diffused light. The amplifier unit 110 is an amplifier which amplifies the amplitude of the detection signal $D_1$ output from the photodetector unit 100 so as to generate the detection signal $D_2$.

The CFD unit 120 is a time-pickoff circuit which generates the start signal $S_1$ at the time when a predetermined time has passed after the level of the detection signal $D_2$ output from the amplifier unit 110 had reached a predetermined ratio of its amplitude. The delay circuit 130 generates the stop signal $S_2$ whose phase is shifted by a predetermined time from the input timing $t_0$ of the trigger signal T input from the trigger circuit 30. The TAC 140 generates the time-correlated signal A having an amplitude proportional to the difference in time between the input timings of the start signal $S_1$ and the stop signal $S_2$ which are output from the CFD unit 120 and the delay circuit 130, respectively.

Based on the information indicative of the measurement start timing contained in the control signal $C_1$ output from the central processing unit 20, the MCA 150 fractions the time-correlated signal A output from the TAC 140 at a predetermined time ($\tau/n$) and sequentially stores thus fractioned signals in an n-piece memory group. Then, the MCA 150 analyzes the pulse-height of the time-correlated signal A and generates the time spectrum data P as frequency distribution of pulse height.

In the following, the action of the measurement apparatus 1 in accordance with this embodiment will be explained.

In the above-configured measurement apparatus 1, as shown in FIG. 3, the central processing unit 20 which has started the predetermined measurement program outputs the control signal $C_1$ indicative of the measurement start timing to each of the trigger circuit 30 and the MCA 150. At this time, based on the control signal $C_1$ output from the central processing unit 20, the trigger circuit 30 outputs the trigger signal T, which becomes an index for the emission timings of the measurement light beams having the n kinds of wavelengths $\lambda_1$ to $\lambda_n$, to each of the first to n-th light sources $40_1$ to $40_n$, control circuit 80, photodetector unit 100, and delay circuit 130. On the other hand, based on the control signal $C_1$ output from the central processing unit 20, the MCA 150 is placed under an input-waiting condition with respect to the time-correlated signal A concerning the measurement light beams having the n kinds of wavelengths $\lambda_1$ to $\lambda_n$.

Subsequently, based on the trigger signal T output from the trigger circuit 30, the first to n-th light sources $40_1$ to $40_n$ pulse-oscillate the measurement light beams having the n kinds of wavelengths $\lambda_1$ to $\lambda_n$ in the same period τ with phases respectively shifted with time 0, τ/n, 2τ/n, ..., and (n−1)τ/n. On the other hand, based on the trigger signal T output from the trigger circuit 30, the control circuit 80 outputs the control signal $C_1$, which generates a Bragg diffraction of deflection angle θ with respect to the measurement light beams, to the wavelength selector unit 90. Also, the delay circuit 130 outputs the stop signal $S_2$, whose phase is shifted by a predetermined time from the trigger signal T output from the trigger circuit 30, to the TAC 140.

Figure 4:
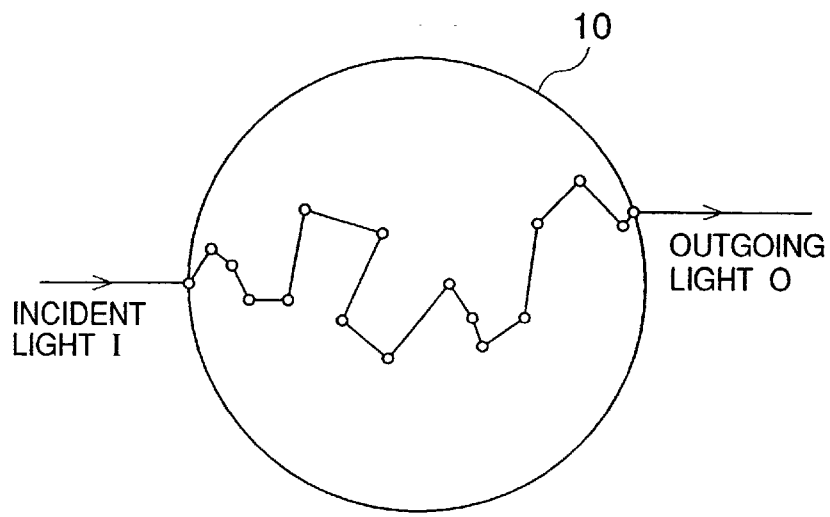
FIG. 4 is a cross-sectional view schematically showing an example of an optical path of measurement light transmitted through a scattering medium in the measurement apparatus shown in FIG. 3.
Figure 5:
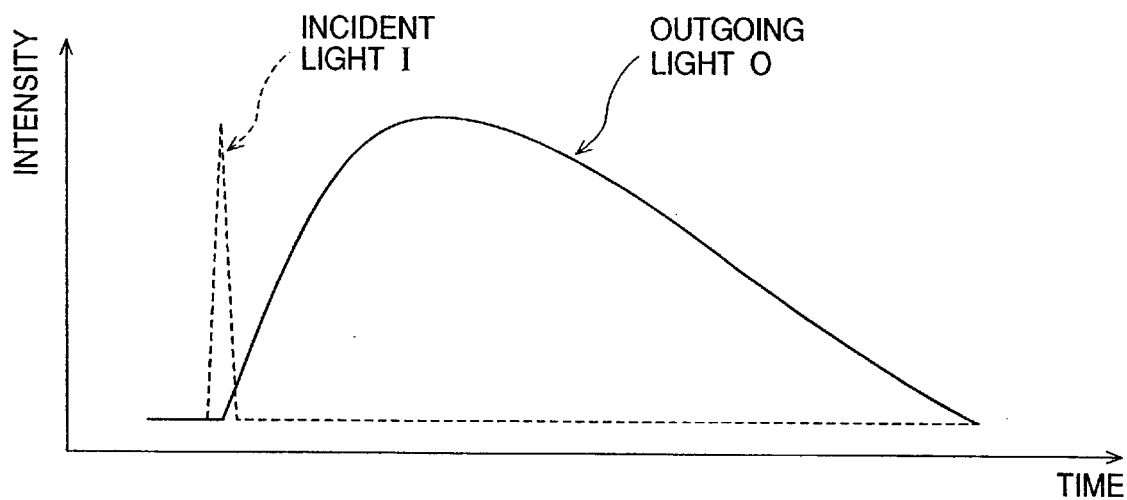
FIG. 5 is a graph showing temporal waveforms of a measurement light pulse entering a scattering medium and the diffused light emitted from the scattering medium in the measurement apparatus shown in FIG. 3.

Here, the measurement light beams sequentially emitted by the first to n-th light sources $40_1$ to $40_n$ irradiate the scattering medium 10 through the irradiation light guide 50 in the form of a spot. As shown in FIG. 4, such a measurement light beam enters the light-entering position of the scattering medium 10 as incident light I and then is diffusively propagated through the scattering medium while being attenuated upon absorbing actions therewithin before being emitted from the light-output position of the scattering medium 10 as outgoing light O. Within the scattering medium 10, the light proceeds along a bent optical path as being randomly scattered by the scattering components constituting the scattering medium 10, while exponentially losing its quantity as being gradually absorbed by the absorbent components constituting the scattering medium 10. Accordingly, as shown in FIG. 5, even when the incident light I is an impulse, the outgoing diffused light O has an extended pulse width since it contains a component which is remarkably delayed from the emission timing of the incident light I due to the multiple scattering.

Here, within the scattering medium 10, based on its random scattering, the light drastically attenuates its density while diffusing into substantially the whole area. However, in FIG. 4, only an example of track of a photon emitted from the light-output position and detected at the light-detection point of the scattering medium 10, namely, an example of track of a photon actually used for measurement is schematically shown. Also, in FIG. 5, in order to compare the respective pulse widths of the incident light I and outgoing light O with each other, they are shown with the same intensity.

Then, as shown in FIG. 3, the diffused light sequentially emitted from the scattering medium 10 are detected by the detection light guide 60 and guided to the optical shaper 70, where they are subsequently converged and guided to the wavelength selector unit 90. Based on the control signal $C_2$ output from the control circuit 80, the wavelength selector unit 90 alternately generates, in synchronization with the emission timings for the measurement light beams having the n kinds of wavelengths $\lambda_1$ to $\lambda_n$, the ultrasonic waves having the n kinds of wavelengths $\lambda_1'$ to $\lambda_n'$. Accordingly, among the diffused light entering the wavelength selector unit 90, only the diffused light having the wavelength $\lambda_i$ corresponding to the wavelength $\lambda_i'$ of the ultrasonic wave are subjected to the Bragg diffraction of deflection angle θ, thereby sequentially being emitted to the photodetector unit 100.

Based on the trigger signal T output from the trigger circuit 30, the photodetector unit 100 sequentially detects the diffused light having the n kinds of wavelengths $\lambda_1$ to $\lambda_n$ sequentially entering it by way of the wavelength selector unit 90 and converts them to the electric signal $D_1$. Sampling timing $t_{si}$ with respect to the diffused light having the wavelength $\lambda_i$ among the diffused light having the n kinds of wavelengths $\lambda_1$ to $\lambda_n$ is defined with respect to the input timing $t_0$ of the trigger signal T output from the trigger circuit 30 or the emission timing $t_{oi}$ for the measurement light beam having the wavelength $\lambda_i$ in the i-th light source $40_i$ by the following equation (4):

$$t_{si} = t_0 + m - \tau + \tau(i-1)/n + \Delta t \qquad (4)$$
$$= t_{oi} + \Delta t$$

wherein Δt is 1/integer of the period τ of each of the measurement light beams having the n kinds of wavelengths $\lambda_1$ to $\lambda_n$. Then, the photodetector unit 100 outputs the detection signal $D_1$, which has an amplitude at a degree corresponding to the single photo-electron level.

Figures 6A, 6B, 6C:
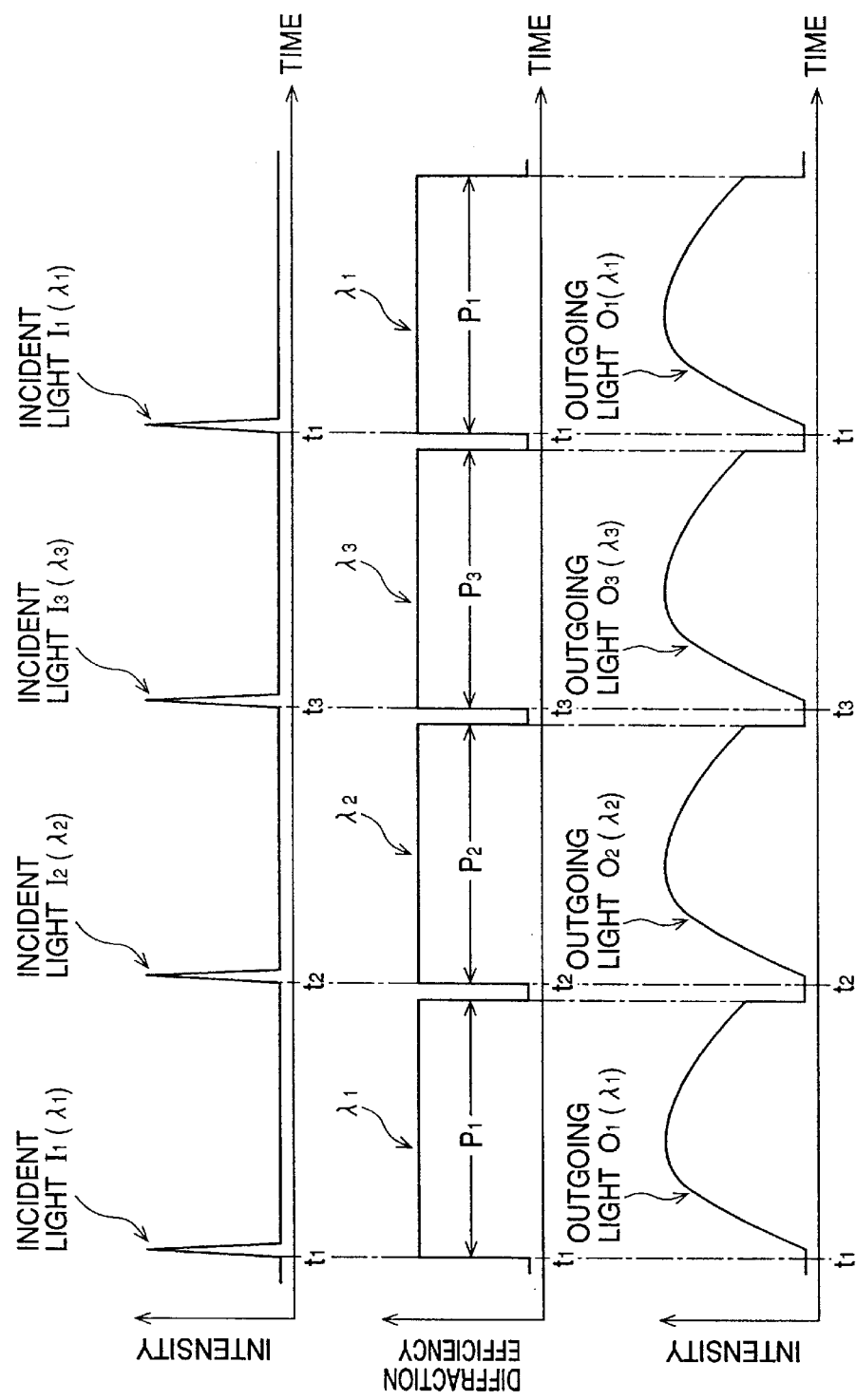
FIGS. 6A, 6B, and 6C are graphs respectively showing temporal waveforms of measurement light beams entering a scattering medium with their wavelengths being sequentially changed for every single pulse, a time-transmittance characteristic at a wavelength selector unit into which the diffused light emitted from the scattering medium enters, and temporal waveforms of the diffused light passed through the wavelength selector unit in the measurement apparatus shown in FIG. 3.

For example, in the case of n=3, as shown in FIG. 6A, the measurement light beams sequentially entering the scattering medium 10 become a time series in which a series of pulses formed by incident light $I_1$ having a wavelength $\lambda_1$, incident light $I_2$ having a wavelength $\lambda_2$, and incident light $I_3$ having a wavelength $\lambda_3$ arranged in terms of time are cycled. In this case, as shown in FIG. 6B, the diffraction efficiency at which the Bragg diffraction of deflection angle θ is generated at the wavelength selector unit 90 reaches an effective value only with respect to the light having the wavelength $\lambda_j$ during the period $p_j$ between the emission timing $t_j$ for the incident light $I_j$ having the wavelength $\lambda_j$ and the emission timing $t_{j+1}$ for the incident light $I_{j+1}$ having the wavelength $\lambda_{j+1}$. Here, j is an integer not less than 1 but not more than 3, $t_4=t_1$, and $p_4=p_1$.

As shown in FIG. 7, the diffused light sequentially emitted from the scattering medium 10 become a time series in which a series of outgoing light $O_1$ having a wavelength $\lambda_1$, outgoing light $O_2$ having a wavelength $\lambda_2$, and outgoing light $O_3$ having a wavelength $\lambda_3$ arranged in terms of time are cycled. However, since the outgoing light $O_j$ contains a component which is delayed from the emission timing $t_{j+1}$ for the incident light $I_{j+1}$ in terms of time, the outgoing light $O_j$ and outgoing light $O_{j+1}$ which are close to each other in terms of time contain components which have mixed with each other within the scattering medium 10. Accordingly, if the measurement apparatus 1 is not provided with the wavelength selector unit 90, a base-line shift occurring due to such mixed components will cause an error when the optical absorption and optical scattering characteristics of the scattering medium 10 are calculated.

By contrast, since the measurement apparatus 1 of the present invention is provided with the wavelength selector unit 90, as shown in FIG. 6C, in the diffused light sequentially entering the photodetector unit 100 from the scattering medium 10, the outgoing light $O_j$ does not contain other components. Accordingly, the outgoing light $O_j$ and outgoing light $O_{j+1}$ which are close to each other in terms of time do not mixed each other within the scattering medium 10, thereby preventing the base-line shift from occurring.

Subsequently, the amplifier unit 110 outputs the detection signal $D_2$, in which the amplitude of the detection signal $D_1$ output from the photodetector unit 100 is amplified, to the CFD unit 120. At the moment when a predetermined time has passed after the level of the detection signal $D_1$ output from the photodetector unit 100 had reached a predetermined ratio of its amplitude, the CFD unit 120 outputs the start signal $S_1$ to the TAC 140. The TAC 140 outputs the time-correlated signal A, which has an amplitude proportional to the difference in time between the input timings of the start signal $S_1$ and the stop signal $S_2$ respectively output from the CFD unit 120 and the delay circuit 130, to the MCA 150. The MCA 150 fractions the time-correlated signal A output from the TAC 140 at a predetermined time (τ/n) and sequentially stores thus fractioned signals in the n-piece memory group, while analyzing the pulse-height of the time-correlated signal A, thereby outputting n kinds of the time spectrum data P, which respectively correspond to the n kinds of wavelengths $\lambda_1$ to $\lambda_n$, to the central processing unit 20 as a frequency distribution of the pulse-height of the time-correlated signal A.

The n kinds of the time spectrum data P respectively corresponding to the n kinds of wavelengths $\lambda_1$ to $\lambda_n$ can be measured with respect to two kinds of the light-entering position to light-output position distances $\rho_1$ and $\rho_2$, which are different from each other, when at least one of the irradiation light guide 50 and the detection light guide 60 is moved with respect to the surface of the scattering medium 10. Therefore, the MCA 150 outputs 2 n kinds of time spectrum data P, which respectively correspond to the measurement light beams having the n kinds of wavelengths $\lambda_1$ to $\lambda_n$ with respect to the two kinds of the light-entering position to light-output position distances $\rho_1$ and $\rho_2$, to the central processing unit 20. The central processing unit 20 analyzes the 2 n kinds of time spectrum data P output from the MCA 150 so as to calculate, for example, the optical absorption coefficient, optical scattering coefficient, and optical absorbent component concentration of the scattering medium 10.

More specifically, the central processing unit 20 analyzes the time spectrum data P on the basis of the optical diffusion theory. The findings concerning the optical diffusion theory are described in detail in such literatures as "Medical Physics, vol. 19, no. 14, pp. 879–888, 1992". In the following, the principle of measuring the optical absorption and optical scattering characteristics of the scattering medium 10 will be explained.

First, the optical diffusion equation concerning a measurement light beam having wavelength $\lambda$ can be defined with respect to photon fluence rate $\phi(r,t)$ and photon source rate $S(r,t)$ corresponding to position r and time t by the following equation (5):

$$\frac{1}{c} \frac{\partial}{\partial t} \phi(r,t) - D(\lambda)\nabla^2\phi(r,t) + \mu_a(\lambda)\phi(r,t) = S(r,t) \tag{5}$$

wherein:

$\phi(r,t)$: photon fluence rate [mm$^{-2}$·sec$^{-1}$], $D(\lambda)$: optical diffusion coefficient [mm], $\mu_a(\lambda)$: optical absorption coefficient [mm$^{-1}$], c: light velocity in the medium [mm·sec$^{-1}$], and $S(r,t)$: photon source rate [mm$^{-3}$·sec$^{-1}$]

The light speed c is defined in response to the refractive index of the scattering medium 10.

Since the measurement light beam is oscillated like an impulse here, the photon source rate $S(r,t)$ can be expressed as a delta function. Therefore, the optical diffusion expression concerning the measurement light beam entering the scattering medium 10 so as to correspond to the origin (r=0) and the initial time (t=0) is defined by the following equation (6):

$$\frac{1}{c} \frac{\partial \phi(r,t)}{\partial t} - D(\lambda)\nabla^2\phi(r,t) + \mu_a(\lambda)\phi(r,t) \tag{6}$$
$$= \delta(0) - \delta(0)$$

Here, among various optical constants used in equation (6), there are relationships defined by the following two equations (7) and (8):

$$D(\lambda) = [3\{\mu_a(\lambda) + \mu_{ts}(\lambda)\}]^{-1} \tag{7}$$

$$\mu_{ts}(\lambda) = (1-g)\mu_s(\lambda) \tag{8}$$

wherein:

$\mu_{ts}(\lambda)$: transport optical scattering coefficient [mm$^{-1}$], $\mu_s(\lambda)$: optical scattering coefficient [mm$^{-1}$], and g: mean value of $\cos\beta$ with respect to scattering angle $\beta$ Also, in cases where axis of coordinate $\rho$ is set on and along the surface of the scattering medium 10, while axis of-coordinate z which is set along the normal with respect to the surface of the scattering medium 10 so as to be directed thereinto, the boundary condition of the optical diffusion equation indicated by equation (6) can be approximately realized when mean diffusion length $z_0$ is used to assume that a negative point light source is at a position ($\rho=0$, $z=-z_0$). Therefore, the solution of the optical diffusion equation is defined as optical intensity I at a position ($\rho$,0) on the surface of the scattering medium 10 at time t by the following equation (9):

$$I(\rho,0,t) = \{4\pi D(\lambda)\cdot c\}^{-3/2}\cdot t^{-5/2}\cdot\exp\{-\mu_s(\lambda)\cdot c\cdot t\}\cdot z_0\cdot\exp[-(z_0^2+\rho^2)/\{4D(\lambda)\cdot c\cdot t\}] \tag{9}$$

wherein:

$I(\rho,0,t)$: optical intensity [mm$^{-2}$·sec$^{-1}$]

On the other hand, mean optical path length L of the measurement light beam entering the scattering medium 10 so as to correspond to the origin (r=0) and the initial time (t=0) is defined with respect to light-entering position to light-output position distance P of the scattering medium 10 as expressed by the following equation (10):

The findings concerning such a mean optical path length are described in detail in such literatures as "Phys. Med. Biol., vol. 37, no. 7, pp. 1531≠1560, 1992".

$$L(\rho) = \frac{c \cdot \int_0^\infty t \cdot I(\rho,0,t)dt}{\int_0^\infty I(\rho,0,t)dt} \tag{10}$$

Here, based on the above two equations (9) and (10), the mean optical path length of the measurement light beam is expressed by the following equation (11):

$$L(\rho) = (3/2)\{\mu_a(\lambda) + \mu_{ts}(\lambda)\}(\rho^2 + z_0^2)/ \tag{11}$$
$$[1 + \{3(\rho^2 + z_0^2)(\mu_a(\lambda)^2 +$$
$$\mu_a(\lambda) - \mu_{ts}(\lambda))\}^{1/2}]$$

or $$L(\rho) = (3/2)(\rho^2 + z_0^2)[\mu_a(\lambda) + \mu_{ts}(\lambda)]/$$
$$\{1 + \sqrt{\rho^2 + z_0^2}$$
$$\sqrt{3\mu_a(\lambda)[\mu_a(\lambda) + \mu_{ts}(\lambda)]} \}$$

Therefore, when two kinds of time spectrum data P corresponding to the two kinds of the light-entering position to light-output position distances $\rho_1$ and $\rho_2$ concerning the measurement light beam having the wavelength of $\lambda$ are input into equation (10), two kinds of mean optical lengths $L(\rho_1)$ and $L(\rho_2)$ can be calculated. These two kinds of mean optical path lengths $L(\rho_1)$ and $L(\rho_2)$ are input into equation (11) to form simultaneous equations, which can be solved to calculate the optical absorption coefficient $\mu_a(\lambda)$ and transport optical scattering coefficient $\mu_{ts}(\lambda)$. Accordingly, when the two kinds of time spectrum data P corresponding to the two kinds of the light-entering position to light-output position distances $\rho_1$ and $\rho_2$ concerning each of the measurement light beams respectively having the n kinds of wavelengths $\lambda_1$ to $\lambda_n$ are similarly analyzed, n kinds of optical absorption coefficients $\mu_a(\lambda_1)$ to $\mu_a(\lambda_n)$ and n kinds of transport optical scattering coefficients $\mu_{ts}(\lambda_1)$ to $\mu_{ts}(\lambda_n)$ can be calculated.

Further, based on Beer-Lambert's law, the optical absorption coefficient $\mu_a$ of the scattering medium 10 with respect to the measurement light beam having the wavelength of $\lambda$ is defined with respect to the (n–1) kinds of optical absorbent components $A_1$ to $A_{n-1}$ as expressed by the following equation (12):

$$\mu_a(\lambda) = \epsilon_{A1}(\lambda)[A_1] + \epsilon_{A2}(\lambda)[A_2] + \ldots + \epsilon_{An-1}(\lambda)[A_{n-1}] + \alpha(\lambda) \tag{12}$$

wherein:

$\epsilon_{Ak}(\lambda)$: molar extinction coefficient of optical absorbent component $A_k$ [mm$^{-1}$·mM$^{-1}$],

[$A_k$]: molar concentration of optical absorbent component $A_k$ [mM], and $\alpha(\lambda)$: background optical absorption term Here, k is an integer not less than 1 but not more than n-1.

Therefore, in cases where, while n kinds of wavelengths $\lambda_1$ to $\lambda_n$ which make n kinds of background optical absorption terms $\alpha(\lambda_1)$ to $\alpha(\lambda_n)$ coincide with each other are selected beforehand as the wavelengths of the measurement light beams, molar extinction coefficients $\epsilon_{A1}(\lambda_1)$ to $\epsilon_{An-1}(\lambda_1)$, $\epsilon_{A1}(\lambda_2)$ to $\epsilon_{An-1}(\lambda_2)$, ..., and $\epsilon_{A1}(\lambda_n)$ to $\epsilon_{An-1}(\lambda_n)$ of the (n-1) kinds of optical absorbent components $A_1$ to $A_n$ with respect to the measurement light beams having the n kinds of wavelengths $\lambda_1$ to $\lambda_n$ are respectively measured, these n(n-1) kinds of the molar extension coefficients $\epsilon_{A1}(\lambda_1)$ to $\epsilon_{An-1}(\lambda_1)$, $\epsilon_{A1}(\lambda_2)$ to $\epsilon_{An-1}(\lambda_2)$, ..., and $\epsilon_{A1}(\lambda_n)$ to $\epsilon_{An-1}(\lambda_n)$ together with the n kinds of optical absorption coefficients $\mu_a(\lambda_1)$ to $\mu_a(\lambda_n)$ can be input into equation (12) to form simultaneous equations, which can be solved to calculate molar concentrations [$A_1$] to [$A_{n-1}$] of the (n-1) kinds of the optical absorbent components $A_1$ to $A_{n-1}$.

In this manner, the central processing unit 20 can analyze the 2 n kinds of the time spectrum data P output from the MCA 150 so as to calculate, as the optical absorption and optical scattering characteristics of the scattering medium 10, the n kinds of optical absorption coefficients $\mu_a(\lambda_1)$ to $\mu_a(\lambda_n)$, n kinds of transport optical scattering coefficients $\mu_{ts}(\lambda_1)$ to $\mu_{ts}(\lambda_n)$, and molar concentrations [$A_1$] to [$A_{n-1}$] of the (n-1) kinds of the optical absorbent components $A_1$ to $A_{n-1}$.

Second Embodiment

Figure 8:
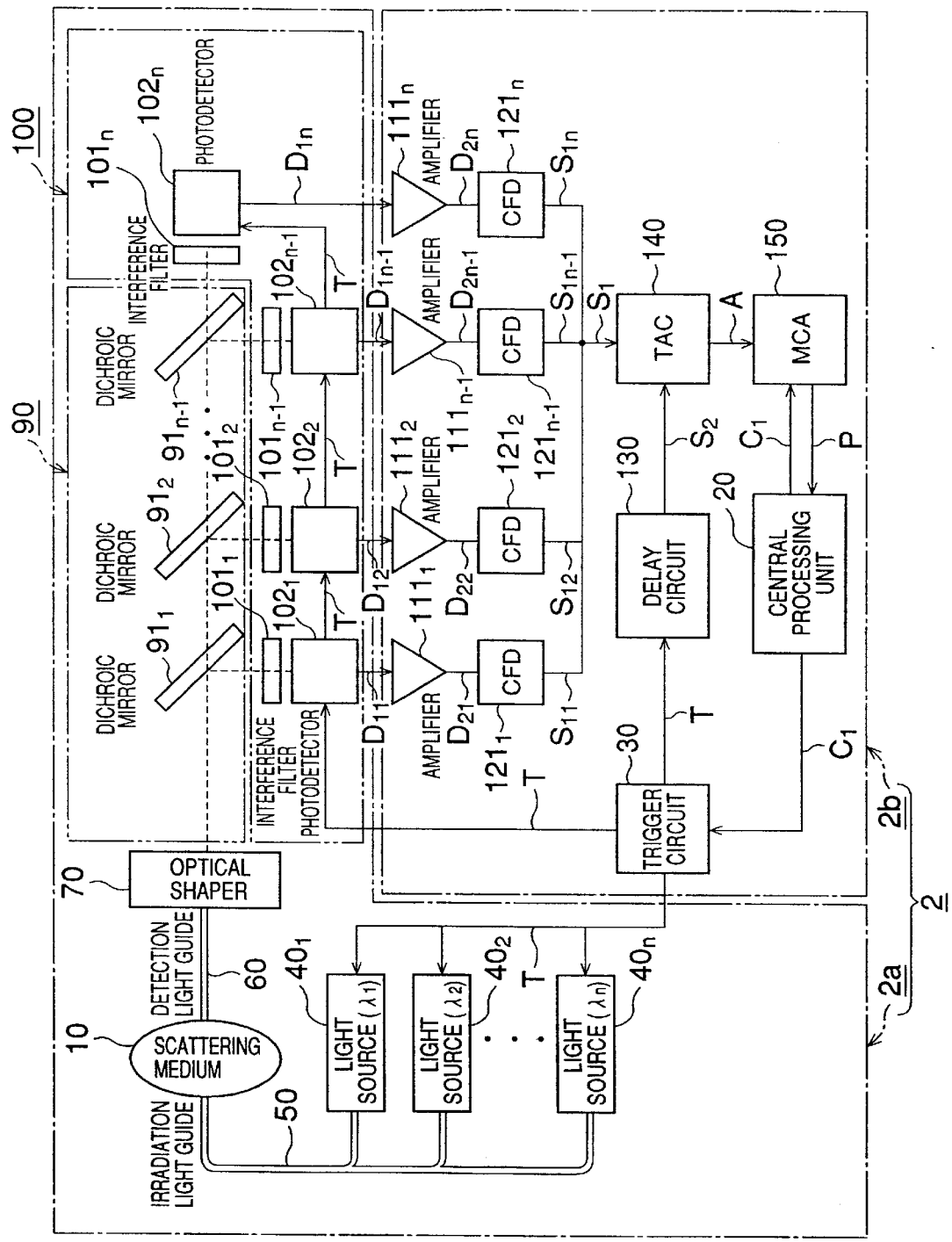
FIG. 8 is a block diagram showing a configuration of the measurement apparatus in accordance with another embodiment of the present invention.

As shown in FIG. 8, a measurement apparatus 2 of this embodiment is configured similarly to the measurement apparatus 1 of the first embodiment. However, this measurement apparatus 2 lacks the control circuit 80 while the internal configurations of its wavelength selector unit 90, photodetector unit 100, amplifier unit 110, and CFD unit 120 are altered.

Here, the wavelength selector unit 90 comprises first to (n-1)-th dichroic mirrors $91_1$ to $91_{n-1}$ serially disposed along the optical axis of the diffused light emitted from the optical shaper 70 in order to selectively extract, in a sequential manner, diffused light having n kinds of wavelengths $\lambda_1$ to $\lambda_n$ from the diffused light sequentially entering the wavelength selector unit 90 from the optical shaper 70. These first to (n-1)-th dichroic mirrors $91_1$ to $91_{n-1}$ have threshold wavelengths, which are set in ascending or descending order so as to reflect or transmit the diffused light sequentially emitted from the optical shaper 70, respectively positioned between neighboring wavelengths close to each other in ascending or descending order among the n kinds of wavelengths $\lambda_1$ to For example, as shown in FIG. 9, the first to (n-1)-th dichroic mirrors $91_1$ to $91_{n-1}$ have (n-1) kinds of wavelength-transmittance distributions $d_1$ to $d_{n-1}$ which exhibit maximum transmittance values with respect to light having wavelengths longer than those near the wavelengths of (n-1) kinds of wavelengths $\lambda_1$ to $\lambda_{n-1}$, respectively. Namely, among the first to (n-1)-th dichroic mirrors $91_1$ to $91_{n-1}$, the h-th dichroic mirror $91_h$ reflects the light component having a wavelength shorter than that near wavelength $\lambda_h$ contained in the measurement light beam entering from the (h-1)-th dichroic mirror $91_{h-1}$ so as to output it to h-th interference mirror $101_h$ which will be explained later, while transmitting a light component having a wavelength longer than that near the wavelength $\lambda_h$ so as to output it to the (h+1)-th dichroic mirror $91_{h+1}$. Here, h is an integer not less than 1 but not more than n-1. The n kinds of wavelengths $\lambda_1$ to $\lambda_n$ are set in ascending order.

The first dichroic mirror 913 transmits, among the diffused light sequentially entering it by way of the optical shaper 70, a light component having a wavelength longer than that near the wavelength $\lambda_1$, while reflecting a light component having a wavelength near the wavelength $\lambda_1$ toward the first interference filter $101_1$. Also, the h-th dichroic mirror $91_h$ transmits, among the diffused light sequentially entering it through the (h-1)-th dichroic mirror $91_{h-1}$, a light component having a wavelength longer than that near the wavelength $\lambda_{h-1}$ so as to emit it to the h-th interference filter $101_h$.

The photodetector unit 100 comprises the first to n-th interference filters $101_1$ to $101_n$ which are disposed in parallel along the optical axes of the light components emitted from the first to (n-1)-th dichroic mirrors $91_1$ to $91_{n-1}$ constituting the wavelength selector unit 90, in order to precisely filter the diffused light having the n kinds of wavelengths $\lambda_1$ to $\lambda_n$ from among the diffused light respectively reflected (or transmitted in the case of the wavelength $\lambda_n$) by the first to (n-1)-th dichroic mirrors $91_1$ to $91_{n-1}$ as well as first to n-th photodetectors $102_1$ to $102_n$ which are disposed in parallel along the optical axes of the light components emitted from the first to (n-1)-th dichroic mirrors $91_1$ to $91_{n-1}$ in order to convert the diffused light respectively entering them by way of the first to n-th interference filters $101_1$ to $101_n$ into n kinds of detection signals $D_{11}$ to $D_{1n}$ which are then output.

The first to (n-1)-th interference filters $101_1$ to $101_{n-1}$ are respectively disposed in the optical axes of the diffused light reflected by the first to (n-1)-th dichroic mirrors $91_1$ to $91_{n-1}$, whereas the n-th interference filter $101_n$ is disposed in the optical axis of the diffused light transmitted through the n-th dichroic mirror $91_n$. These first to n-th interference filters $101_1$ to $101_n$ respectively have transmittance center wavelengths, which are set in ascending or descending order so as to transmit the diffused light emitted from the first to (n-1)-th dichroic mirrors $91_1$ to $91_{n-1}$, coinciding with the n kinds of wavelengths $\lambda_1$ to $\lambda_n$.

The first to n-th photodetectors $102_1$ to $102_n$ are photomultiplier tubes which, based on the trigger signal T output from the trigger circuit 30, detect the diffused light sequentially entering them by way of the first to n-th interference filters $101_1$ to $101_n$ and then convert them to detection signals, thereby generating the n kinds of detection signals $D_{11}$ to $D_{1n}$. In order to favorably detect the respective diffused light having the n kinds of wavelengths $\lambda_1$ to $\lambda_n$, the first to n-th photodetectors $102_1$ to $102_n$ preferably have relatively large spectral sensitivity characteristic and gain. Also, in order to favorably perform the time-resolved measurement of the diffused light, they preferably have a response frequency as high as possible.

The amplifier unit 110 is constituted by first to n-th amplifiers $111_1$ to $111_n$ which are disposed in parallel downstream of the first to n-th photodetectors $102_1$ to $102_n$, respectively, in order to amplify the n kinds of the detection signals $D_{11}$ to $D_{1n}$ output from the first to n-th photodetectors $102_1$ to $102_n$ constituting the photodetector unit 100, thereby outputting n kinds of detection signals $D_{21}$ to $D_{2n}$. These first to n-th amplifiers $111_1$ to $111_n$ are amplifiers which respectively amplify the amplitudes of the n kinds of the detection signals $D_{11}$ to $D_{1n}$ output from the first to n-th photodetectors $102_1$ to $102_n$, thereby generating the n kinds of the detection signals $D_{21}$ to $D_{2n}$.

The CFD unit 120 is constituted by first to n-th CFD $121_1$ to $121_n$ which are disposed in parallel downstream of the first to n-th amplifiers $111_1$ to $111_n$ constituting the amplifier unit 110, respectively, in order to detect the levels of the n kinds of the detection signals $D_{21}$ to $D_{2n}$ which are output from the first to n-th amplifiers $111_1$ to $111_n$, thereby outputting n kinds of start signals $S_{11}$ to $S_{1n}$ as the start signal $S_1$. These first to n-th CFD $121_1$ to $121_n$ are time-pickoff circuits which respectively generate the n kinds of the start signals $S_{11}$ to $S_{1n}$ at the moment when a predetermined time has passed after the levels of the n kinds of the detection signals $D_{21}$ to $D_{2n}$ output from the first to n-th amplifiers $111_1$ to $111_n$ had reached a predetermined ratio of their amplitudes.

In the following, the action of the measurement apparatus 2 in accordance with this embodiment will be explained.

In the above-configured measurement apparatus 2, as shown in FIG. 8, the central processing unit 20 which has started the predetermined measurement program outputs the control signal $C_1$ indicative of the measurement start timing to each of the trigger circuit 30 and the MCA 150. At this time, based on the control signal $C_1$ output from the central processing unit 20, the trigger circuit 30 outputs the trigger signal T, which becomes an index for the emission timings of the measurement light beams having the n kinds of wavelengths $\lambda_1$ to $\lambda_n$, to each of the first to n-th light sources $40_1$ to $40_n$, photodetector unit 100, and delay circuit 130. On the other hand, based on the control signal $C_1$ output from the central processing unit 20, the MCA 150 is placed under an input-waiting condition with respect to the time-correlated signal A concerning the measurement light beams having the n kinds of wavelengths $\lambda_1$ to $\lambda_n$.

Subsequently, based on the trigger signal T output from the trigger circuit 30, the first to n-th light sources $40_1$ to $40_n$ pulse-oscillate the measurement light beams having the n kinds of wavelengths $\lambda_1$ to $\lambda_n$ in the same period $\tau$ with phases respectively shifted with time $0, \tau/n, 2\tau/n, \ldots$, and $(n-1)\tau/n$. On the other hand, the delay circuit 130 outputs the stop signal $S_2$, whose phase is shifted by a predetermined time from the trigger signal T output from the trigger circuit 30, to the TAC 140.

Here, the measurement light beams sequentially emitted by the first to n-th light sources $40_1$ to $40_n$ are converged into a spot by the irradiation light guide 50 and irradiate the scattering medium 10. The measurement light beams sequentially entering the light-entering position of the scattering medium 10 are diffusively propagated through the scattering medium 10 while being attenuated upon absorbing actions therewithin. Then, the diffused light sequentially emitted from the light-output position of the scattering medium 10 are detected by the detection light guide 60 and guided to the optical shaper 70, where they are subsequently converged and guided to the wavelength selector unit 90.

As the diffused light sequentially entering the wavelength selector unit 90 sequentially pass through the first to (n–1)-th dichroic mirrors $91_1$ to $91_{n-1}$, a light component having a wavelength shorter than that near the wavelength $\lambda_1$, a light component having a wavelength longer than that near the wavelength $\lambda_1$ but shorter than that near the wavelength $\lambda_2, \ldots$, and a light component having a wavelength longer than that near the wavelength $\lambda_{n-2}$ but shorter than that near the wavelength $\lambda_{n-1}$ are sequentially reflected and respectively guided to the first to (n–1)-th interference filters $101_1$ to $101_{n-1}$ constituting the photodetector unit 100. The diffused light transmitted through the (n–1)-th dichroic mirror $91_{n-1}$ has a wavelength longer than that near the wavelength $\lambda_n$ and is guided to the n-th interference filter $101_n$ constituting the photodetector unit 100.

In the photodetector unit 100, the diffused light entering the first to n-th interference filters $101_1$ to $101_n$ are respectively filtered as the diffused light having one of the n kinds of wavelengths $\lambda_1$ to $\lambda_n$ and then guided to the first to n-th photodetectors $102_1$ to $102_n$. Based on the trigger signal T output from the trigger circuit 30, the first to n-th photodetectors $102_1$ to $102_n$ sequentially detect the diffused light having the n kinds of wavelengths $\lambda_1$ to $\lambda_n$ respectively entering them by way of the first to n-th interference filters $101_1$ to $101_n$ and then convert the diffused light detected into the n kinds of the detection signals $D_{11}$ to $D_{1n}$ to be output to the first to n-th amplifiers $111_1$ to $111_n$ which constitute the amplifier unit 110.

For example, in the case of n=3, as shown in FIG. 6A, the measurement light beams sequentially entering the scattering medium 10 become a time series in which a series of pulses formed by incident light $I_1$ having a wavelength $\lambda_1$, incident light $I_2$ having a wavelength $\lambda_2$, and incident light $I_3$ having a wavelength $\lambda_3$ arranged in terms of time are cycled.

As shown in FIG. 7, the diffused light sequentially emitted from the scattering medium 10 become a time series in which a series of outgoing light $O_1$ having a wavelength $\lambda_1$, outgoing light $O_2$ having a wavelength $\lambda_2$, and outgoing light $O_3$ having a wavelength $\lambda_3$ arranged in terms of time are cycled. However, since the outgoing light $O_j$ contains a component which is delayed from the emission timing $t_{j+1}$ for the incident light $I_{j+1}$ in terms of time, the outgoing light $O_j$ and outgoing light $O_{j+1}$ are close to each other in terms of time and are mixed each other within the scattering medium 10. Accordingly, if the measurement apparatus 2 is not provided with the wavelength selector unit 90, a baseline shift occurring due to such mixed components will cause an error when the optical absorbing and optical scattering characteristics of the scattering medium 10 are calculated.

By contrast, since the measurement apparatus 2 of the present invention is provided with the wavelength selector unit 90, as shown in FIG. 6C, the diffused light respectively entering the first to n-th photodetectors $102_1$ to $102_n$ from the scattering medium 10 are fractioned into the n kinds of wavelengths $\lambda_1$ to $\lambda_n$. Accordingly, the outgoing light $O_j$ does not contain a component which is delayed from the emission timing $t_{j+1}$ for the incident light $I_{j+1}$ in terms of time. Therefore, the outgoing light $O_j$ and outgoing light $O_{j+1}$ which are close to each other in terms of time do not contain components which have mixed each other within the scattering medium 10, thereby preventing the baseline shift from occurring. Here, j is an integer not less than 1 but not more than 3, $t_4=t_1$, and $p_4=p_1$.

Subsequently, the first to n-th amplifiers $111_1$ to $111_n$ respectively output the n kinds of the detection signals $D_{21}$ to $D_{2n}$, in which the amplitudes of the n kinds of the detection signals $D_{11}$ to $D_{1n}$ respectively output from the first to n-th photodetectors $102_1$ to $102_n$ are amplified, to the first to n-th CFD $121_1$ to $121_n$ which constitute the CFD unit 120. At the moment when a predetermined time has passed after the levels of the n kinds of the detection signals $D_{21}$ to $D_{2n}$ output from the first to n-th amplifiers $111_1$ to $111_n$ had reached a predetermined ratio of their amplitudes, the first to n-th CFD $121_1$ to $121_n$ output the n kinds of the start signals $S_{11}$ to $S_{1n}$ to the TAC 140 as the start signal $S_1$.

The TAC 140 outputs the time-correlated signal A, which has an amplitude proportional to the difference in time between the input timings of the start signal $S_1$ and the stop signal $S_2$ respectively output from the CFD unit 120 and the delay circuit 130, to the MCA 150. The MCA 150 fractions the time-correlated signal A output from the TAC 140 at a predetermined time ($\tau/n$) and sequentially stores thus fractioned signals in the n-piece memory group, while analyzing the wave height value of the time-correlated signal A, thereby outputting n kinds of the time spectrum data P, which respectively correspond to the n kinds of wavelengths $\lambda_1$ to $\lambda_n$, to the central processing unit 20 as a frequency distribution of the wave height values of the time-correlated signal A.

The n kinds of the time spectrum data P respectively corresponding to the n kinds of wavelengths $\lambda_1$ to $\lambda_n$ can be measured with respect to two kinds of the light-entering position to light-output position distances $\rho_1$ and $\rho_2$ when at least one of the irradiation light guide 50 and the detection light guide 60 is moved with respect to the surface of the scattering medium 10. Therefore, the MCA 150 outputs 2 n kinds of time spectrum data P, which respectively correspond to the measurement light beams having the n kinds of wavelengths $\lambda_1$ to $\lambda_n$ with respect to the two kinds of the light-entering position to light-output position distances $\rho_1$ and $\rho_2$, to the central processing unit 20. The central processing unit 20 analyzes the 2 n kinds of time spectrum data P output form the MCA 150 so as to calculate, for example, the optical absorption coefficient, optical scattering coefficient, and optical absorbent component concentration of the scattering medium 10.

Here, without being restricted to the foregoing embodiments, the present invention can be subjected to various modifications. For example, in the foregoing embodiments, the wavelength selector unit comprises an acousto-optic modulator or multiple-stage dichroic mirror group which selectively extracts only diffused light having a predetermined wavelength from among diffused light having a plurality of wavelengths. However, as long as the wavelength can be similarly selected with respect to the diffused light, various means such as prism and directional coupler can be used as the wavelength selector unit.

Also, in the foregoing embodiments, a plurality of the light sources comprise laser diodes which emit measurement light beams having wavelengths different from each other at emission timings different from each other. However, as long as the setting of the wavelength and control of the emission timings in the measurement light beams can be similarly effected, various means such as light emitting diode can be used as a plurality of the light sources.

Further, in the foregoing embodiments, the photodetectors comprise photomultiplier tubes which respectively detect the diffused light having wavelengths different from each other. However, as long as both spectral sensitivity characteristic and gain are similarly high, various means such as avalanche photodiode, streak camera, photoelectric tube, and pin-type photodiode can be used.

Also, in the foregoing embodiments, the number of kinds of wavelengths contained in the measurement light beams irradiating a subject scattering medium is set at a value which is greater than the number of kinds of the optical absorbent components contained in the scattering medium by 1. However, when the background absorption within the subject scattering medium is so small that it can be neglected, the number of kinds of wavelengths contained in the measurement light beams can be set at a value coinciding with the number of kinds of the optical absorbent components contained in the scattering medium.

Further, in the foregoing embodiments, the subject scattering medium is a living tissue. However, various kinds of other substances may be used as the subject scattering medium as long as they contain optical absorbent components having absorbance values which are relatively high with respect to the measurement light beams, which are emitted from a plurality of light sources, and different from each other.

As explained in detail in the foregoing, in the measurement apparatus of the present invention, the measurement light beams having wavelengths different from each other sequentially emitted at emission timings different from each other in a periodic manner from a light source or light sources are irradiated into a scattering medium by way of the irradiation light guide and, after being diffusively propagated through the scattering medium, are guided to the wavelength selector unit. Then, the wavelength selector unit selectively extracts, in a sequential manner, the diffused light having predetermined wavelengths. Accordingly, even when the diffused light sequentially emitted from the scattering medium has a pulse width greater than that at the time of incident due to random scattering and thus contains light components mixed within the scattering medium, the diffused light sequentially emitted from the wavelength selector unit do not contain such mixed light components.

As a result, since no base-line shift occurs due to the mixed light components in the diffused light sequentially entering the photodetector unit, even when the interval of the emission timings for the measurement light beams is shortened to such an extent that the diffused light emitted from the scattering medium may contain the mixed light components, the time-response characteristic of the diffused light can be accurately measured by the signal processing system. Accordingly, as the signal processing system analyzes the time-response characteristic of the diffused light measured by the photodetector unit, internal information in the scattering medium such as its optical scattering and optical absorption characteristics can be accurately calculated. Here, when the above-mentioned measurement is repeated at different times while the light-entering and light-output positions of the scattering medium are fixed, changes in various characteristic values concerning the optical scattering and optical absorption characteristics over time can be obtained. Further, when the above-mentioned measurement is repeated while the light-entering and light-output positions of the scattering medium are scanned, spatial distributions of various characteristic values concerning the optical scattering and optical absorption characteristics can be obtained.

Since the measurement light beams having wavelengths different from each other are sequentially emitted at emission timings different from each other in a periodic manner, the time required for measuring the time-response characteristics of the measurement light beams with respect to the scattering medium is determined depending on the duration of diffused light to be detected at each wavelength of the measurement light beams, thereby alleviating the restriction on the number of kinds of wavelength set in the measurement light beams. Further, since the wavelength selector unit extracts only a light component having a predetermined wavelength from light in which the measurement light beams having wavelengths different from each other are mixed within the medium, the emission frequency for each wavelength of the measurement light beams has an upper limit higher than that conventionally available. Accordingly, in the measurement apparatus of the present invention, it is unnecessary for the emission timings for the measurement light beams to have such a large interval that the diffused light emitted from the scattering medium does not contain the mixed light components. Therefore, the time required for measuring the time-response characteristic of the diffused light with respect to the scattering medium can be greatly shortened as compared with the conventional techniques.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 202115/1995 (7-202115) filed on Aug. 8, 1995, is hereby incorporated by reference.

What is claimed is:

1. A measurement apparatus for measuring internal characteristics of a scattering medium comprising:

a plurality of light sources which emit a plurality of measurement light beams having a plurality of wavelengths different from each other;

an irradiation light guide for causing said measurement light beams to be incident on the scattering medium;

a wavelength selector unit which selectively extracts diffused light having a particular wavelength from diffused light having mutually interfering light components corresponding to said measurement light beams which have been diffusively propagated through said scattering medium;

a photodetector unit for measuring a time-response characteristic of said diffused light extracted by said wavelength selector unit; and a signal processing system which drives said plurality of light sources so as to sequentially cause said measurement light beams to be incident on the scattering medium respectively with emission timings different from each other, and which controls a measurement action of said photodetector unit corresponding to said emission timings such that time-response characteristics of said diffused light are sequentially measured, while analyzing the time-response characteristics measured by said photodetector unit so as to calculate the internal information in said scattering medium.

2. A measurement apparatus according to claim 1, wherein said wavelength selector unit comprises an acousto-optic modulator, said acousto-optic modulator generating an ultrasonic wave based on a control signal output from said signal processing system and changing a wavelength of said ultrasonic wave in synchronization with the emission timing of said measurement light beam so as to diffract said diffused light by a deflection angle which corresponds to ratio of the wavelength of said diffused light to that of said ultrasonic wave; and said photodetector unit comprises a photodetector, said photodetector performing, based on a control signal output from said signal processing system, detecting said diffused light which has been diffracted by the predetermined deflection angle by said acousto-optic modulator and then converting said diffused light thus detected so as to effect a time-resolved measurement.

3. A measurement apparatus according to claim 1, wherein said wavelength selector unit comprises a plurality of dichroic mirrors, said dichroic mirrors being serially disposed in an optical path of said diffused light guided from said scattering medium to said photodetector unit such that threshold wavelengths thereof are respectively positioned between neighboring wavelengths of said diffused light and set in ascending or descending order; and said photodetector unit comprises a plurality of interference filters and a plurality of photodetectors, said interference filters respectively having transmittance center wavelengths coinciding with wavelengths of said diffused light entering said interference filters from said dichroic mirrors, whereas said photodetectors respectively performing, based on a control signal output from said signal processing system, detecting said diffused light entering said photodetectors from said interference filters and then converting said diffused light thus detected so as to effect a time-resolved measurement.

4. A measurement apparatus according to claim 1, further comprising:

a detection light guide for guiding said diffused light which has been diffusively propagated through said scattering medium to said wavelength selector unit; and an optical shaper which is optically connected to said detection light guide and converges said diffused light so as to be guided to said wavelength selector unit.

5. A measurement apparatus according to claim 1, wherein said light source is a group of light sources which respectively emit, based on a control signal output from said signal processing system, said measurement light beams having a plurality of wavelengths whose number is not smaller than that of kinds of optical absorbent components contained in said scattering medium and which have absorption coefficients different from each other with respect to said optical absorbent components.

* * * * *